United States Patent
Baudry et al.

(10) Patent No.: US 6,461,375 B1
(45) Date of Patent: Oct. 8, 2002

(54) METHOD AND APPARATUS FOR ELECTROMAGNETIC STIMULATION OF THE SKIN FOR TREATING PATHOLOGICAL CONDITIONS

(76) Inventors: Alain Baudry, 55 Boulevard de la Cayolle, 13009 Marseille (FR); Michel Marignan, 15 Chemin de la Pageotte, 13011 Marseille (FR)

(*) Notice: Subject to any disclaimer, the term of this patent is extended or adjusted under 35 U.S.C. 154(b) by 0 days.

(21) Appl. No.: 09/445,646
(22) PCT Filed: Jun. 13, 1997
(86) PCT No.: PCT/FR97/01074
§ 371 (c)(1), (2), (4) Date: Dec. 9, 1999
(87) PCT Pub. No.: WO98/56457
PCT Pub. Date: Dec. 17, 1998

(51) Int. Cl.$^7$ .................................................. A61N 1/00
(52) U.S. Cl. .......................................................... 607/1
(58) Field of Search ............................ 607/1, 2, 61, 65, 607/69, 76

(56) References Cited

U.S. PATENT DOCUMENTS

| | | | |
|---|---|---|---|
| 4,793,325 A | * 12/1988 | Cadossi et al. | |
| 4,895,149 A | 1/1990 | Morez | 1289/419 |
| 5,158,473 A | 10/1992 | Takahashi et al. | |
| 5,158,526 A | 10/1992 | Bricot | 600/9 |

FOREIGN PATENT DOCUMENTS

| | | |
|---|---|---|
| DE | 3326513 | 7/1983 |
| EP | A 65 473 | 5/1982 |
| EP | 0065 473 A1 | 11/1982 |
| EP | 89907175.7 | 12/1989 |
| EP | 0 447 568 | 9/1991 |
| FR | 75 04116 | 6/1976 |
| FR | 76 32116 | 5/1977 |
| FR | 76 36152 | 6/1978 |
| FR | 79 04486 | 11/1980 |
| FR | 81 09663 | 5/1981 |
| FR | 80 23007 | 4/1982 |
| FR | 83 14020 | 8/1983 |
| FR | 2620943 A1 | 3/1989 |
| FR | 2625105 A1 | 6/1989 |
| FR | 2 687 075 | 2/1992 |
| FR | 88 08347 | 8/1997 |
| WO | WO 89/12435 | 12/1987 |
| WO | WO 91/17737 | 11/1991 |
| WO | 95/03850 | 2/1995 |

OTHER PUBLICATIONS

Lexikon Elektronik, Physik Verlag 1978, p. 563, Fig. 2.
International Search Report dated Feb. 23, 1998.
English translation of International Preliminary Examination Report dated Jun. 13, 1997.

* cited by examiner

Primary Examiner—Scott M. Getzow
(74) Attorney, Agent, or Firm—Cohen, Pontani, Lieberman & Pavane

(57) ABSTRACT

The present invention relates to a novel method and device for electromagnetic stimulation of the skin for the purpose of modifying a physiological condition or performing treatment of a given pathology, and also to an electronic device enabling said method to be implemented. The device is characterized in that it comprises electronic elements imparting oscillatory behavior thereto at at least one resonant frequency, said resonance being induced by electromagnetic induction external to the device. A particular embodiment of the device is a passive electronic circuit that does not include any source of energy, characterized in that it comprises in series a self-inductor (1), a capacitor (2), and a resistor (3).

10 Claims, 2 Drawing Sheets

METHOD AND APPARATUS FOR ELECTROMAGNETIC STIMULATION OF THE SKIN FOR TREATING PATHOLOGICAL CONDITIONS

FIELD OF THE INVENTION

The present invention relates to a novel method and apparatus for electromagnetic stimulation of the skin in order to modify a physiological condition or to treat a given pathological condition, and it also relates to electronic apparatus enabling the method to be implemented.

STATE OF THE ART

There exist numerous techniques for treating various pathological conditions by external stimulation of specific points or zones of the body. Presently known kinds of stimulation are performed by apparatuses using a variety of techniques, amongst which mention can be made of the needles that are traditionally used in acupuncture, mechanical vibration, electrical currents, electromagnetic radiation, magnets, light radiation (non-coherent visible light, laser light, ultraviolet light, and infrared light, . . . ), optical filters, etc.

Numerous stimulation points or areas are used that are distributed over substantially over all of the surface of the body, and in this context, non-limiting mention can be made of the following: the points known for use in acupuncture, in reflexotherapy, in auriculo-medicine, and in podologcial apparatuses.

To illustrate the variety and the state of those techniques, various patents that are representative in this field can be mentioned:

1) The French patent filed on Feb. 10, 1975 under the No. 75 04116 by the German company ELMATRON GmbH relating to "Apparatus for encouraging the healing of cells of human or animal organisms by means of electromagnetic pulses". That apparatus emits electromagnetic waves at a frequency that is not stated precisely (high frequencies), but in the form of repetitive pulses themselves at frequencies in the range 0 to 1000 Hz.

2) The German patent of Oct. 29, 1975, extended to France on Oct. 25, 1976 under the No. 76 32116 by MESSERSCHMITT-BOLKOW-BLOHM relating to "Apparatus making use of the action of light for therapeutic treatments similar to acupuncture". It relates specifically to projecting low power laser radiation that is pulsed by means of a shutter at a frequency of 2 Hz to 20 Hz, thereby stimulating specified points (light spots that are about 1 mm in diameter), as determined in acupuncture and giving the same effects as are obtained using needles.

3) The French patent filed on Nov. 24, 1976 under the No. 76 32152 by Mr. Pierre NOGIER, concerning "A method and apparatus for local stimulation by electromagnetic radiation". The radiation is produced by a beam of infrared radiation that is at least semicoherent, having a fundamental frequency of 73 Hz and including numerous harmonics, and illuminating selected points of the body (unspecified) and no details are given as to the effects obtained.

4) The French patent filed on Feb. 15, 1979 under the No. 79 04486 by Mr. P. NOGIER, describing "A method and apparatus for magnetic treatment of living organisms". He describes a device of the Polaroid glass type that is suitable for polarizing light and that is interposed between a source of magnetic flux of the magnet type and the organism to be treated; the polarized flux then penetrates deep into the organism without losing its polarization, unlike polarized light.

Apparatuses using that method are sold under the name "POLARTRON" and act on the nervous system to calm pain (ears, scars, etc. . . . ).

5) The French patent filed on Oct. 28, 1980 under the No. 80 23007 by Mr. Christian C. MARET relating to "Light-emitting apparatus having a physiological effect via the skin". That apparatus is quite complex, since it comprises a flashing light emitter having a period of 2 to 6 seconds, passing successively and in this order through a colored filter assembly, and then through layers of tissue impregnated with dilute active substances.

That device is suitable for fixing to the wrist or the ankle of the user and enables a plurality of therapeutic actions to be combined by an appropriate selection of filters associated with the active substances that are diluted and rendered dynamic by using the methods of HAHNEMANN.

6) The French patent filed on May 13, 1981 under the No. 81 09663 and extended to Europe under the No. 82430023.1 by Mr. Bernard BRICOT, describing "A foot device for treating reflex zones of the feet, and in particular troubles and affections due to rachidian unbalance". The idea is to stimulate the reflex zones of the feet, and is rather general since the device claimed can cover the entire surface of the sole of the foot by means of a polarizer constituted by at least two plates or sheets of a material having a determined molecular or crystal orientation, the plates being superposed in such a manner that their polarization axes are crossed. That device makes use of the same therapeutic principle as the POLARTRON described in Mr. NOGIER's patent, but without an active magnetic source which is toxic if its intensity is too strong, in particular for use on the foot. The therapeutic results are obtained after several months by rebalancing of the spine and by improvement of various functional disturbances relating to statics.

7) The German patent filed on Jul. 22, 1983 under the No. 33 26 513.5 and extended to Europe, including France, by Mr. Volkmar TETZNER, relating to "Irradiation apparatus for photobiological and photochemical treatments". That apparatus has a source of ultraviolet illumination illuminating the skin for treatments, in particular dermatological treatments, via a set of filters placed in pairs in a housing, and suitable for being easily interchanged depending on the treatment.

8) The French patent filed on Aug. 29, 1983 under the No. 83 14020 by Mr. Jean Bernard MOREZ, relating to "Apparatus for non-manual stimulation of points of the cutaneous covering known as acupuncture points". That invention relates to acoustic stimulation modulated at low frequency.

9) The French patent filed on Jun. 17, 1988 under the No. 88 08347 by Messrs. Michel MARIGNAN, Philippe REBOUL, and Philippe SOUVESTRE, relating to "A podological device for correcting troubles and affections of neuromuscular tonus concerning posture". That device is constituted by one or more films acting as optical filters and placed in a solepiece positioned in register with the reflex zone that is to be stimulated.

10) The French patent filed on May 18, 1990 under the No. 90 06241 and then extended internationally on May 14, 1991 under the No. WO 91/17737 by Mr. Sao VU-DINH, relating to "Portable self-contained acupuncture apparatus". That small-sized apparatus contained in a housing of the watch-strap type performs electrical stimulation on points on the inside face of the wrist by applying voltages in the range 1 to 12 volts, for a duration of 0.1 seconds to 2 seconds, and at a repetition frequency of 0.5 Hz to 10 Hz.

11) The European patent filed on Oct. 2, 1990 under the No. 0 447 568 A1 by Messrs. Valery LOBAREV, Sergi SITKO, and Vadim LJUCHENKO and describing "Apparatus for therapy by microwave resonance". That apparatus is constituted by an electromagnetic source operating in the millimeter band (25 GHz to 150 GHz) for stimulating the resonant frequencies of the organism.

Most of those apparatuses or methods make use of respective external active sources, thereby making them more complicated to use (size, weight) and making it impossible for them to be worn on a continuous basis since a power supply is required. In addition, the action thereof can be toxic since the intensity of the radiation can have harmful effects on the organism.

The stimulation is sometimes continuous, but is also often pulsed or modulated by a signal at low frequency.

None of those pieces of equipment has given rise to results that are statistically proven and repeatable.

Several of those apparatuses make use of electromagnetic emissions, particularly in the visible or infrared light spectrum.

Apparatuses of that type are sometimes associated with filters (polarizing or colored) for optimizing the positive effects of the said source, some of which are used directly on the organism (laser, ultraviolet lamp, magnetic field, etc. . . . ).

The filters are added to limit the radiation at source and to allow only the active portion of the flux thereof to pass, which portion is thus reinforced.

Furthermore, those apparatuses are applied to points which are never clearly specified by the inventors, who have generally observed beneficial effects on organisms, but without results or tests that have been proven and described in their inventions, since the results can be very different from one person to another and it is the experience of the user that determines which zones of the body are the most receptive and the treatments that correspond thereto. only a few techniques do not make use of an external active source, such as Mr. BRICOT's invention which uses polarizing plates, and the invention of Messrs. MARIGNAN and SOUVESTRE which uses optical filters, or those using magnets such as the invention of Mr. Edouard LEBART which combines magnets with mechanical stimulation (French patent 2 687 075 of Aug. 13, 1993).

SUMMARY OF THE INVENTION

The method of the present invention is a method for electromagnetic stimulation of the skin applied to a living organism and more particularly the human organism, at certain points or certain areas that are determined by the pathology to be treated, or by the desired physiological modifications, using a resonant electronic device whose resonant frequency(ies) (also referred to as "natural" frequencies) are themselves determined by the looked-for effect expected from the stimulation.

Compared with known methods of stimulation by generating a magnetic field or by emitting electromagnetic waves by means of an active source, thereby transferring energy to the organism, the method of the invention uses the resonant capability of an active or passive device to interact with the organism, mainly by absorbing electromagnetic energy external to the device.

The method thus consists in placing an electronic device at certain locations that are propitious for such stimulation, such that said device under the influence of the magnetic field and the electromagnetic radiation generated by the organism enters into resonance at its natural frequency(ies), which is/are determined depending on the effect looked for on the organism, and the device is made accordingly.

The invention uses electromagnetic coupling between the device of the invention and any structure of the organism capable of interacting with the device by means of said coupling.

The resonance of the circuit as induced by the organism gives rise to a modification in the electromagnetic behavior of the organism, and causes said organism to be stimulated.

The method therefore does not require direct contact with the organism, it can be implemented by means of a device that may possibly be completely passive, i.e. that has no source of energy, thus avoiding any risk of exceeding the energy levels acceptable to the organism.

The advantage of such a method is that it enables stimulation to be performed continuously, where the stimulation is effective while being inoffensive, and can be applied to any point of the body including the sole of the foot, by means of devices of size that is very small, thereby enabling them to be worn continuously and discreetly.

Furthermore, the desired resonant frequency, associated with the pathology being treated, can easily be obtained in a device of the invention, as can all the harmonics of said frequency.

Because of its effective and prolonged action, this stimulation method has shown its effectiveness firstly as a palliative, and then in the longer term as a curative for various pathological conditions.

By way of example, mention can be made of spectacular controlled and measured results obtained on individuals suffering from balance troubles, following severe damage to the inner ear, e.g. to the perilymphatic fistulae.

Another application that has shown the effectiveness of the method and of the device is correcting troubles and affections of neuromuscular tonus concerning posture.

The device of the invention for implementing the above-described method can itself be embodied by one or more electronic circuits exhibiting resonant behavior, together with an element for electromagnetic coupling with the structures concerned of the organism.

Such a circuit has a mode of operation whereby, when it is at resonance, it absorbs energy from the organism which then behaves as a source, said energy being amplified by the fact that this interchange takes place at certain special frequencies of the circuit known as resonant frequencies. This phenomenon is well known and is used both in mechanics and in electronics.

The electromagnetic coupling is obtained by induction by means of a coil type element, or using a dipole type of device.

DESCRIPTION OF A PREFERRED EMBODIMENT

Such devices comprise active or passive electronic components. Such circuits can easily be made using passive components only: capacitors, inductors, resistors.

Components and their values are selected as a function of the biological and medical targets to be achieved which relate to the resonant frequency(ies) and also to the intensity of the coupling.

Figure 1:
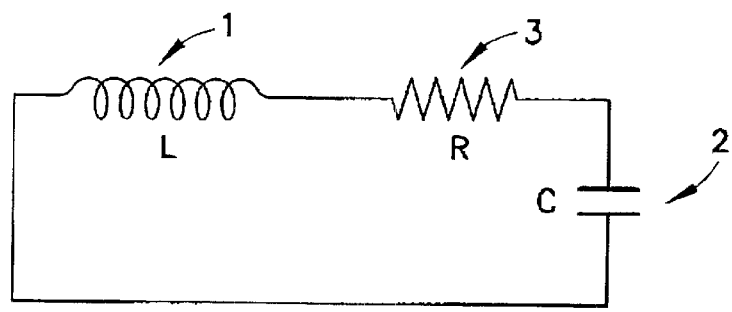
FIG. 1 represents an LRC electronic circuit useful in a device according to the invention.

One of the simplest devices enabling the described method to be implemented comprises a closed circuit in the form of a self-inductor 1 of inductance L that can be made in the form of a few turns of a coil, a capacitor 2 of capacitance C, and a resistor 3 of resistance R (FIG. 1).

To obtain more effective coupling, the inductor should be placed in such a manner that the plane containing the turns is parallel to a plane that is tangential to the surface of the skin at the point that is to be stimulated.

Such a circuit possesses a natural frequency of oscillation F given by:

$$F=1/[2\pi(LC)^{1/2}]$$

An advantageous method of making the inductor, the components involved in both the resonance, and the magnetic coupling with the organism, consists in making a printed circuit on a plane medium 4 which can be rigid or flexible, in which a circuit track having a concentric path implements the nested circular or polygonal turns of the inductor.

In this embodiment, the circuit is placed in such a manner that the printed circuit board is parallel to the surface of the skin, as mentioned above.

Figures 2A, 2B:
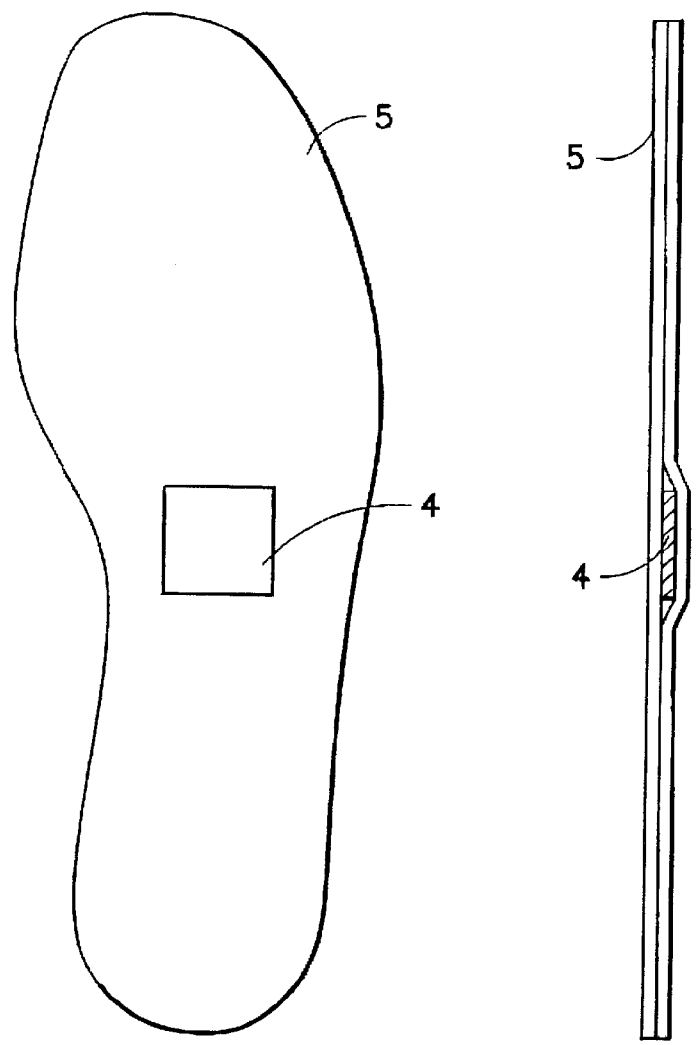
FIG. 2 represents the sole of a shoe wherein a device comprising an LRC circuit is implanted according to the invention.

This embodiment and the positioning of the device can be illustrated by an LRC circuit of the kind described above, having a circular track implemented as concentric turns, situated in the plane of the printed circuit, and implanted in the sole 5 of a shoe (FIG. 2) for placing under the sole of the foot to obtain optimum coupling.

An embodiment of the device as described above is obtained by an LRC circuit that is implemented in the form of a printed circuit whose copper track forms its turns and that has inductance of about 0.5 $\mu$H, associated with a capacitance of about 12 nF, thereby giving a resonant frequency of about 2 MHz.

By way of non-limiting example of an application of the present invention, such a device has been found to be effective in the treatment of vertigo associated with uneasiness in a case of perilymphatic fistulae. Other frequencies are also used for other pathologies, mainly but without being limiting, in the field of frequencies of a few megahertz to a few tens of megahertz.

When the resistance R of the circuit is very small, for example constituted solely by the resistance specific to the tracks of the printed circuit of the device, resonance takes place over a frequency band that is very narrow, it is of large amplitude, and it makes it possible to provide stimulation that is very selective in frequency and very powerful.

However, non-negligible resistance in the circuit constitutes a factor that damps resonance and that enables stimulation to take place more gently.

Figure 3:
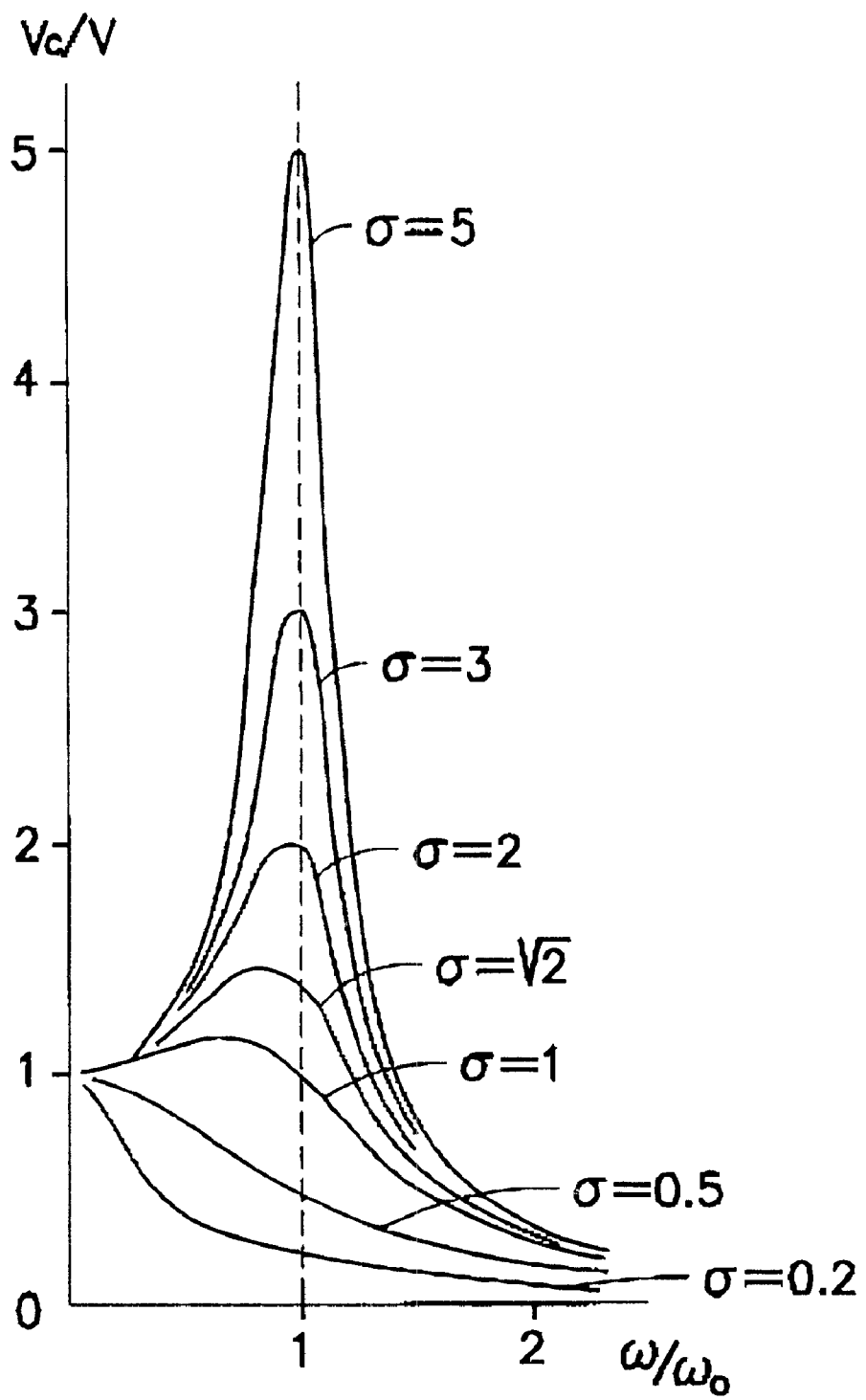
FIG. 3 represents a graph showing the resonance phenomenon of the LRC circuit of the invention.

The graph (FIG. 3) shows the resonance phenomenon for various values of the damping term associated with said resistance.

The magnitude of the amplification factor $V_c/V$ is plotted up the ordinate (i.e. the ratio of the voltage $V_c$ in the circuit to the applied or induced electromagnetic force V) as a function of the angular frequency ratio ($\omega/\omega_0$ plotted along the abscissa (ratio of the angular frequency $\omega$ of the applied electromotive force to the natural frequency of the circuit, $\omega_0=2\pi F$)) for various values of the damping coefficient $\sigma=L\omega_0/R$.

More complex devices of the invention can be made by associating a plurality of circuits of the above type (monomode, i.e. having a single resonant frequency), or by using multimode circuits, thereby enabling the organism to be stimulated at a plurality of frequencies simultaneously.

Finally, more complex stimulation functions can be implemented by associating active components in a resonant circuit.

Similarly, higher level functions can be associated with the device such as functions of the autotest type, and characteristics that vary or that can be modulated over time.

Given the wide variety of points or zones of the organism that can be subjected to stimulation by the method described, the device can be of very small size given the principle on which it is based, and can be inserted in a support that enables it to be held in place at a small distance from a point to be stimulated, but without physical contact being necessary.

Tests have been performed using the supports described below, without that being limiting in any way:
  a shoe sole for foot stimulation (FIG. 2);
  a bracelet for wrist stimulation;
  a headband for head stimulation; and
  an adhesive tape or bandage for other locations.

Naturally, the invention applies in non-limiting manner to the fields of human and veterinary medicine.

What is claimed is:

1. An electromagnetic device for stimulation of the skin at certain points or zones of the organism, comprising electronic components imparting oscillating behavior thereto at at least one resonant frequency, said resonance being induced by electromagnetic induction external to the device.

2. A device according to claim 1, wherein said electronic components comprise a passive resonant circuit at said at least one given frequency, which circuit does not have a source of energy.

3. A device according to claim 2, which is constituted by an electronic circuit comprising a self-inductor, a capacitor, and a resistor, possessing a single natural frequency.

4. A device according to claim 2, wherein the components are disposed and soldered on a plane printed circuit that is rigid or flexible.

5. A device according to claim 1, using elements for electromagnetic coupling with the organism that are of the induction coil type (self-inductance) or of the antenna type (electrical dipole).

6. A device according to claim 5, wherein the self-inductor is constituted by a track of a printed circuit whose path forms a set of nested turns that are circular or polygonal.

7. A device according to claim 1, making use simultaneously of a plurality of resonant frequencies.

8. A device according to claim 1, being incorporated in a support of appropriate material for positioning it correctly relative to the point or zone that is to be stimulated, the support being of the bracelet, band, or sole type.

9. A method for electromagnetic stimulation of the skin at at least one of a point or a zone of the organism for at least one of modifying a physiological condition and treating a pathology, according to which an electronic device that is resonant at least at one given frequency corresponding to the desired treatment is placed close to a predetermined point or zone of the organism, external electromagnetic energy being picked up by said device such that said device resonates at least at said one given frequency and said predetermined point or zone is stimulated by the electromagnetic energy absorbed by the device.

10. The use of a passive LCR electronic circuit having at least one resonant frequency, comprising the step of using the circuit for electromagnetic stimulation of the skin in order to at least one of modifying a physiological condition and treating a pathology.

* * * * *